(12) United States Patent
Werp et al.

(10) Patent No.: US 7,774,046 B2
(45) Date of Patent: Aug. 10, 2010

(54) MAGNETIC NAVIGATION SYSTEM

(75) Inventors: Peter R. Werp, St. Louis, MO (US); Francis M. Creighton, IV, St. Louis, MO (US)

(73) Assignee: Stereotaxis, Inc., St. Louis, MO (US)

(*) Notice: Subject to any disclaimer, the term of this patent is extended or adjusted under 35 U.S.C. 154(b) by 1295 days.

(21) Appl. No.: 10/799,358

(22) Filed: Mar. 12, 2004

(65) Prior Publication Data
US 2004/0249262 A1 Dec. 9, 2004

Related U.S. Application Data

(60) Provisional application No. 60/454,410, filed on Mar. 13, 2003.

(51) Int. Cl.
*A61B 5/05* (2006.01)
(52) U.S. Cl. ............... 600/429; 600/407; 600/410; 600/424; 128/899
(58) Field of Classification Search ........... 600/407, 600/410, 424, 429; 324/318, 319, 200; 128/899
See application file for complete search history.

(56) References Cited

U.S. PATENT DOCUMENTS

| | | | | |
|---|---|---|---|---|
| 4,875,485 | A | * 10/1989 | Matsutani | .......... 600/415 |
| 4,949,043 | A | * 8/1990 | Hillenbrand et al. | ...... 324/320 |
| 5,257,636 | A | 11/1993 | White | |
| 5,312,321 | A | 5/1994 | Holcomb | |
| 5,622,169 | A | 4/1997 | Golden et al. | |
| 5,681,260 | A | 10/1997 | Ueda et al. | |
| 5,689,190 | A | * 11/1997 | Cuppen | .......... 324/319 |

(Continued)

FOREIGN PATENT DOCUMENTS

WO    WO 99/23934    *   5/1999

OTHER PUBLICATIONS

J.M. D. Coey et al., "Construction and Evaluation of Permanent Magnet Variable Flux Sources", 13th Int. Workshop on RE Magnets & their Applications.

*Primary Examiner*—Long V Le
*Assistant Examiner*—Ellsworth Weatherby
(74) *Attorney, Agent, or Firm*—Harness, Dickey & Pierce, P.L.C.

(57) ABSTRACT

A magnetic navigation system for orienting a magnetically responsive device in an operating region in a subject has at least two magnet units and a support for mounting the at least two magnet units for movement relative to the subject, the support supporting the at least two magnet units adjacent the operating region in the subject at locations to apply a magnetic field to the operating region. Each magnet unit includes sing a magnet and a positioner for selectively changing the position of the magnet. The system also includes a control for operating the positioners of each magnet unit to selectively change the positions of the magnets to maintain the magnetic field direction applied to the operating region by the magnets as the locations of the magnet units relative to the operating region change. The system is adapted for implementing a method of navigating according to the present invention in which the magnets in the magnet units are selectively rotated and pivoted to maintain the appropriate magnetic field direction projected by the magnets to maintain the device direction as the magnet units move on the support about the operating region.

15 Claims, 13 Drawing Sheets

U.S. PATENT DOCUMENTS

| | | | |
|---|---|---|---|
| 6,029,081 A * | 2/2000 | DeMeester et al. | 600/410 |
| 6,241,671 B1 * | 6/2001 | Ritter et al. | 600/427 |
| 6,346,814 B1 * | 2/2002 | Carrozzi et al. | 324/318 |
| 6,346,816 B1 * | 2/2002 | Damadian et al. | 324/319 |
| 6,459,924 B1 * | 10/2002 | Creighton et al. | 600/427 |
| 6,522,145 B1 * | 2/2003 | Damadian et al. | 324/318 |
| 6,630,879 B1 | 10/2003 | Creighton, IV et al. | |
| 7,019,610 B2 * | 3/2006 | Creighton et al. | 335/306 |
| 7,264,584 B2 * | 9/2007 | Ritter et al. | 600/1 |
| 7,313,429 B2 * | 12/2007 | Creighton et al. | 600/427 |

* cited by examiner

U.S. 7,774,046 B2

MAGNETIC NAVIGATION SYSTEM

CROSS-REFERENCE TO PREVIOUSLY FILED APPLICATIONS

This invention claims priority of U.S. patent application Ser. No. 60/454,410, filed Mar. 13, 2003, the entire disclosure of which is incorporated herein by reference.

BACKGROUND OF THE INVENTION

This invention relates to methods and apparatus for magnetically navigating magnetically responsive medical devices in an operating region in a subject.

Medicine is increasingly relying on the remote navigation of medical devices in the body to reduce patient trauma, speed recovery, and perform procedures that could not be performed with conventional surgical techniques. Magnetic navigation of medical devices provides fast, simple, and reliable navigation in a subject's body. With the reduced size and increase flexibility of magnetically responsive medical devices, magnetically navigated devices can reach parts of the subjects body that could not be reached with most previously available remote navigation techniques.

Magnetic navigation relies upon external source magnets, either electromagnets, or more recently permanent magnets, to provide a controllable magnetic field in an operating region in a subject to orient a magnetically responsive device in the operating region. A challenge for magnetic navigation is to position the magnet sufficient close to the patient to provide a sufficiently strong field for magnetic navigation, while accommodating patients of varying sizes, leaving room for other medical equipment (particularly imaging equipment), and provide access to the patient.

SUMMARY OF THE INVENTION

Generally, the apparatus and method of this invention employ at least two magnet units movably mounted adjacent (and preferably on opposite sides of) an operating region in a subject for coordinated movement about the operating region. Each magnet unit comprises a magnet and a positioner for changing the position of the magnet, and thus the direction of the magnetic field that the magnet applies to the operating region. The magnets are mounted for coordinated movement about the operating region, so that the magnet units can be positioned close to the operating region, yet be moved out of the way to positions where they still apply a magnetic field to the operating region, when necessary for example to accommodate imaging equipment. The system preferably includes a controller for operating the positioners to maintain the magnetic field direction as the magnet units are moved.

Thus, the invention provides a simple, relatively inexpensive way of applying a magnetic field in a selected direction. The capability of positioning the magnet units close to the operating region allows the magnets to be made smaller and more compact, which in turn means that the positioners can be smaller and less expensive. The smaller, more compact size of the magnets means that they interfere less with access to the patient by medical equipment or personnel, and the ability to move the magnet unit around the operating region allows the magnets to moved out of the way when needed, while still maintaining a magnetic field in the operating region. These and other features and advantages will be in part apparent, and in part pointed out hereinafter.

BRIEF DESCRIPTION OF THE DRAWINGS

Corresponding reference numerals indicate corresponding parts throughout the several views of the drawings.

DETAILED DESCRIPTION OF THE INVENTION

Figure 1:
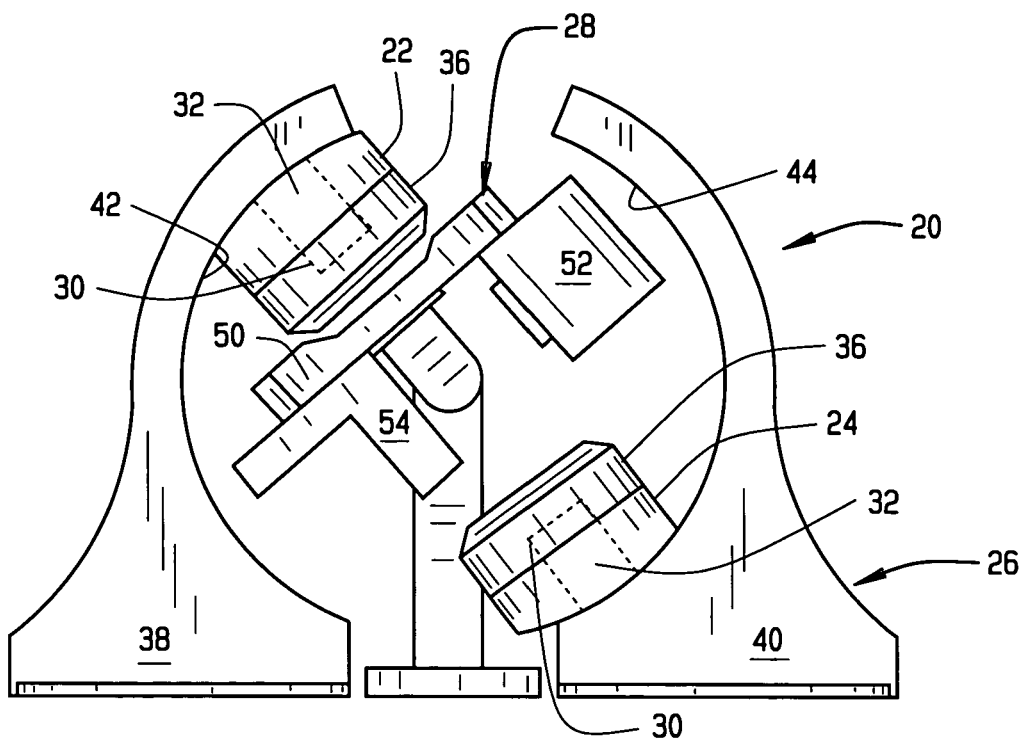
FIG. 1 is a front elevation view of a first embodiment of a magnetic navigation system constructed according to the principles of this invention.
Figure 2:
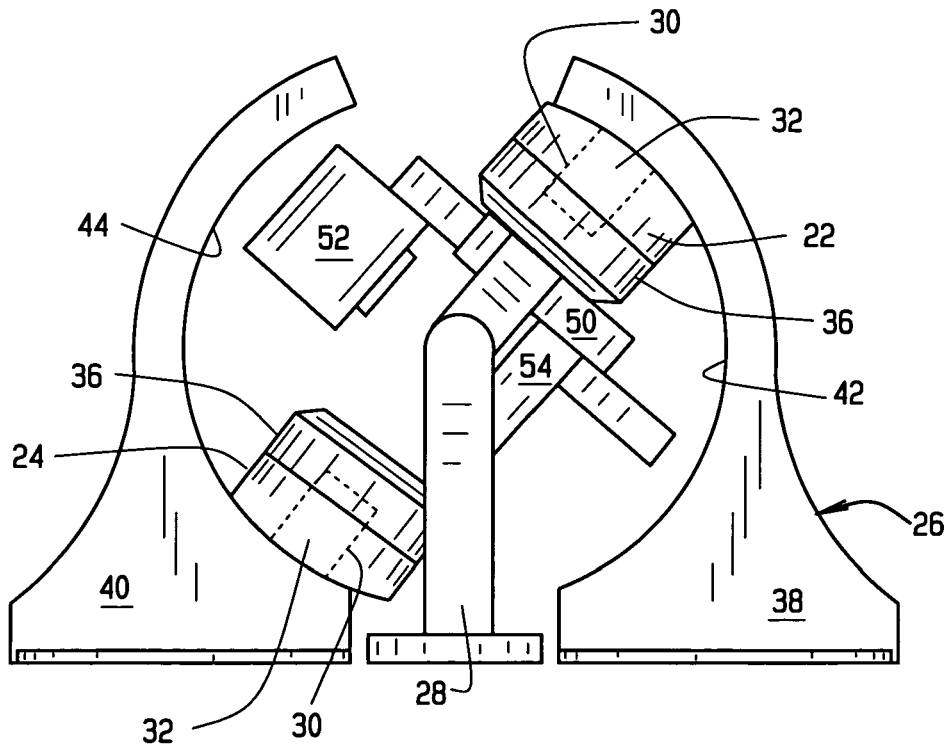
FIG. 2 is a rear elevation view of the magnetic navigation system of the first embodiment.
Figure 4:
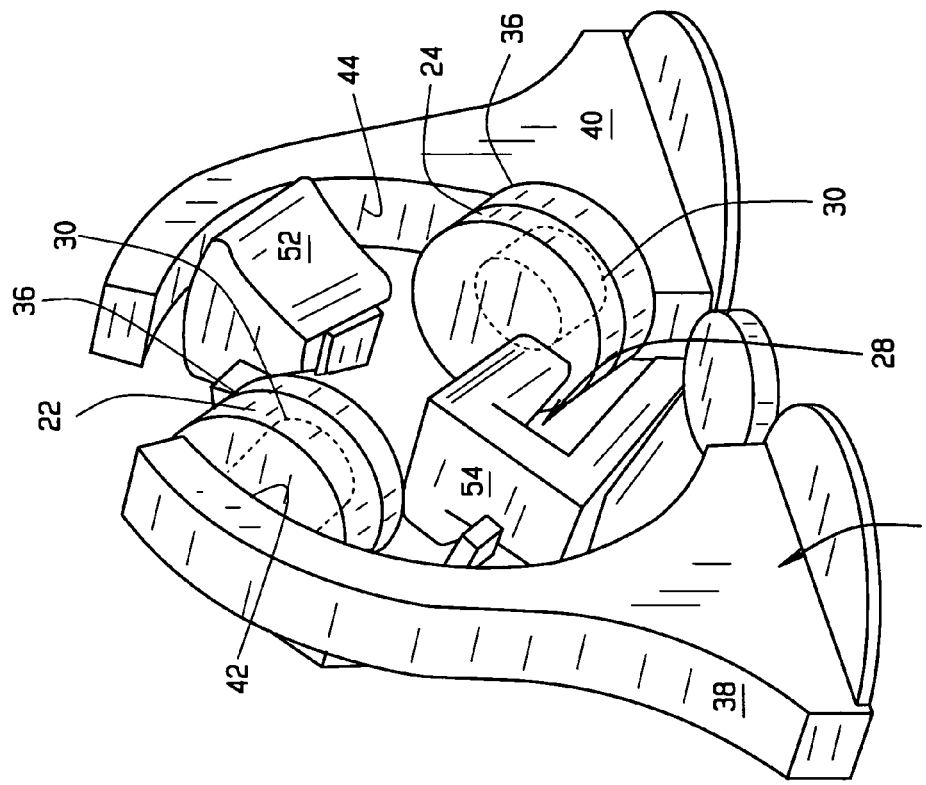
FIG. 4 is a front perspective view of the magnetic navigation system of the first embodiment.
Figure 3:
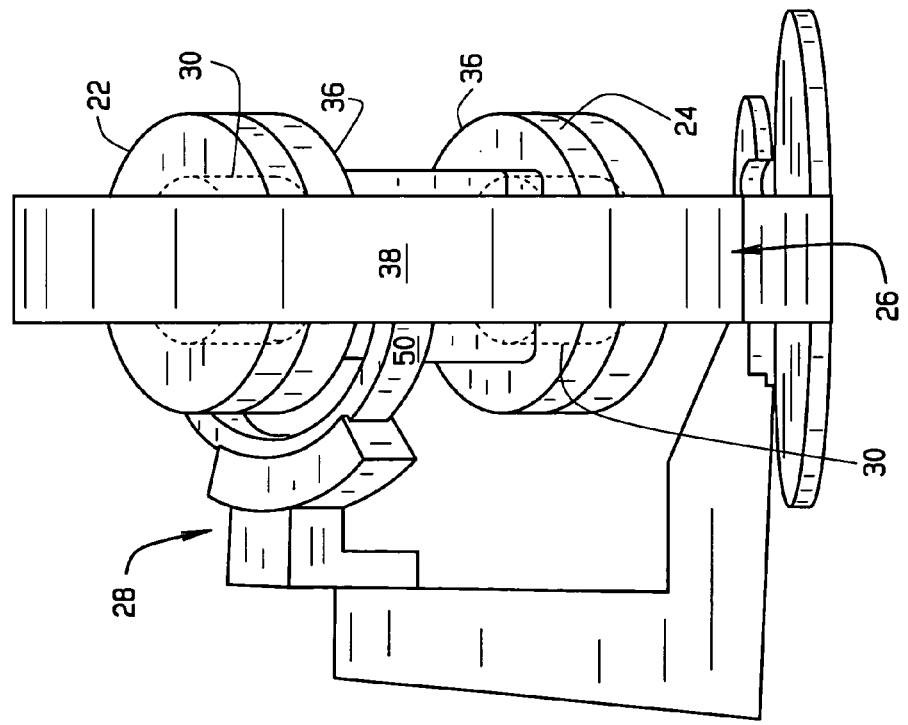
FIG. 3 is a side elevation view of the magnetic navigation system of the first embodiment.
Figure 5:
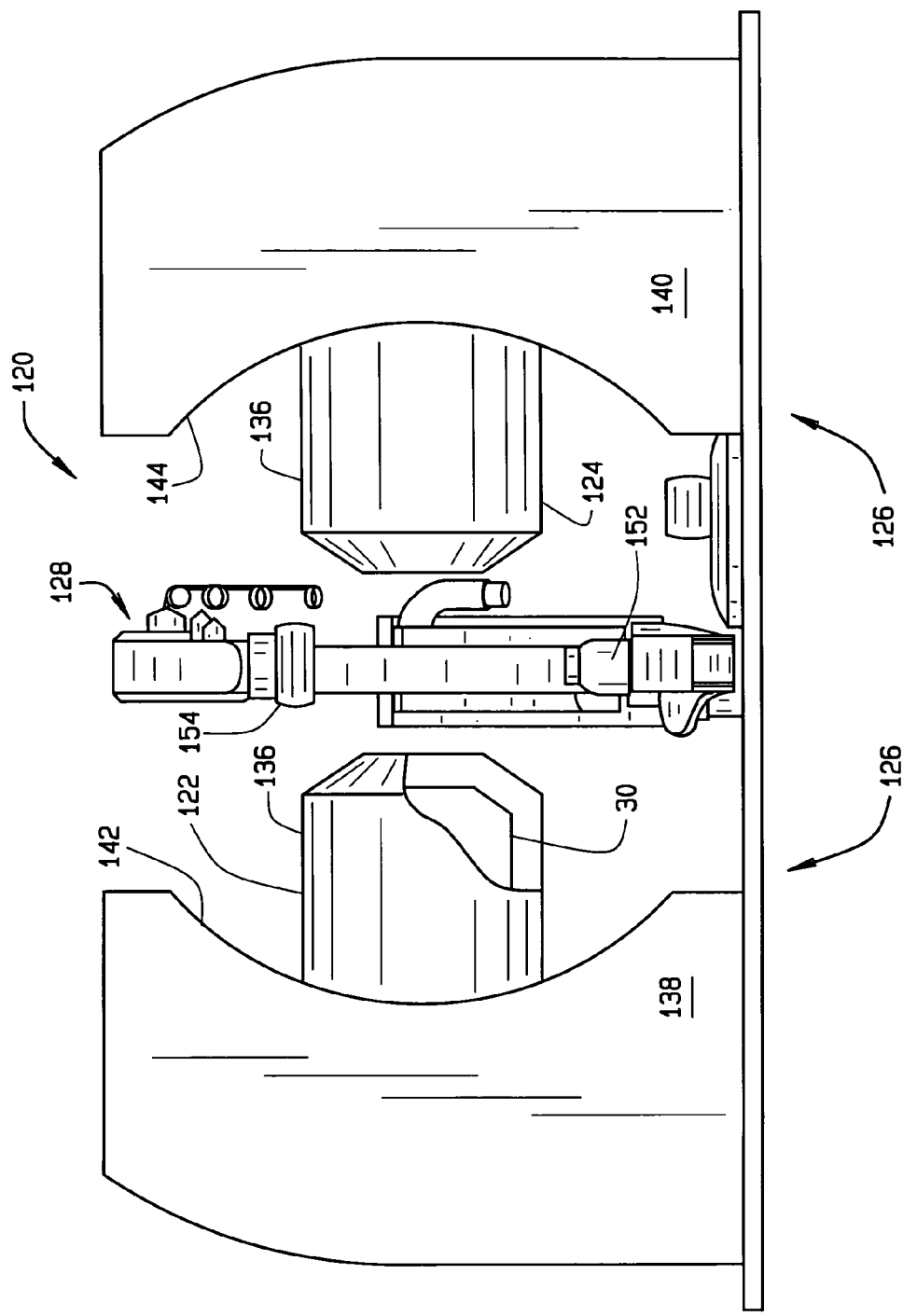
FIG. 5 is a front elevation view of a second embodiment of a magnetic navigation system constructed according to the principles of this invention.
Figure 6:
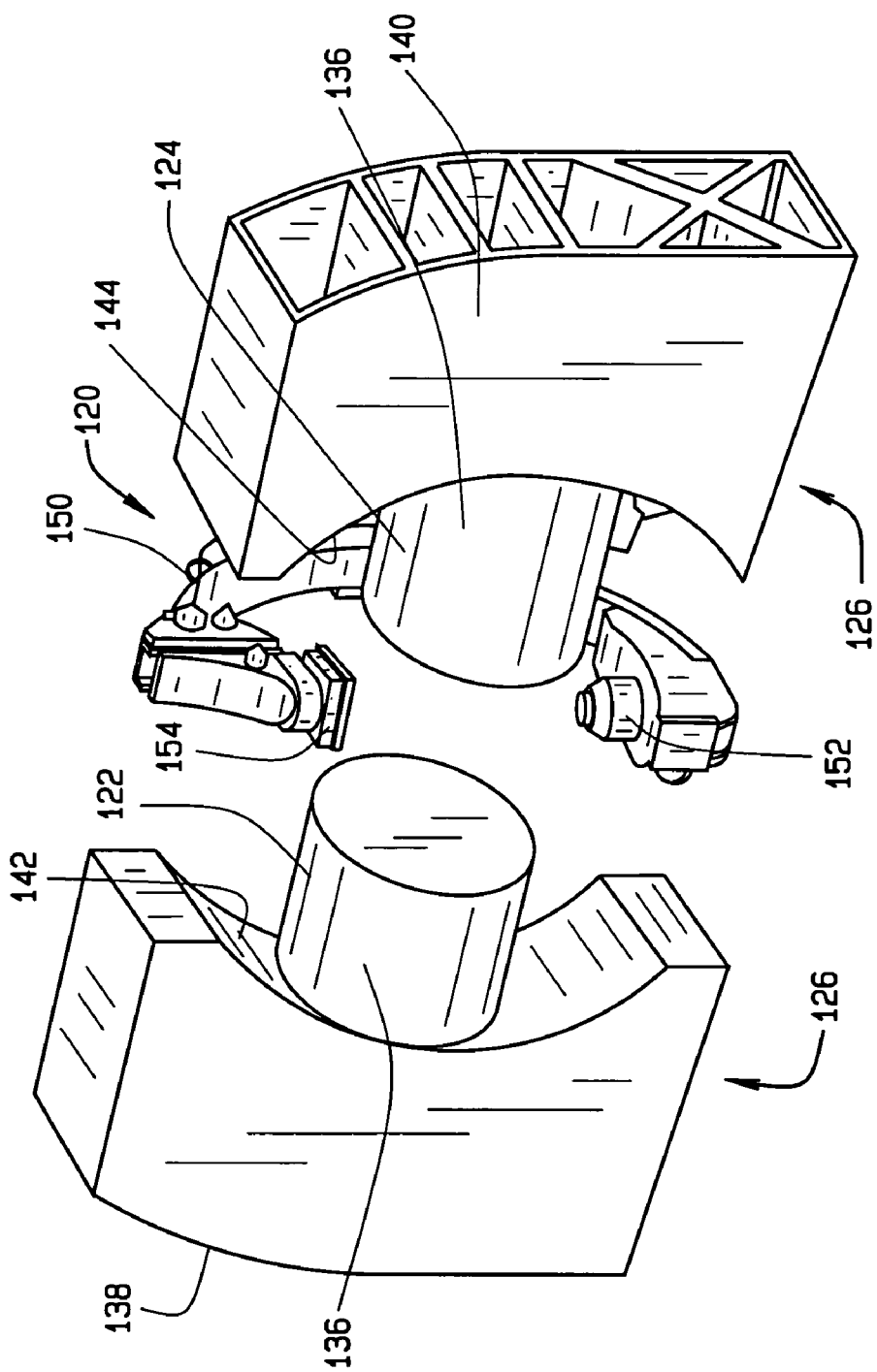
FIG. 6 is a front perspective view of the magnetic navigation system of the second embodiment.
Figure 7:
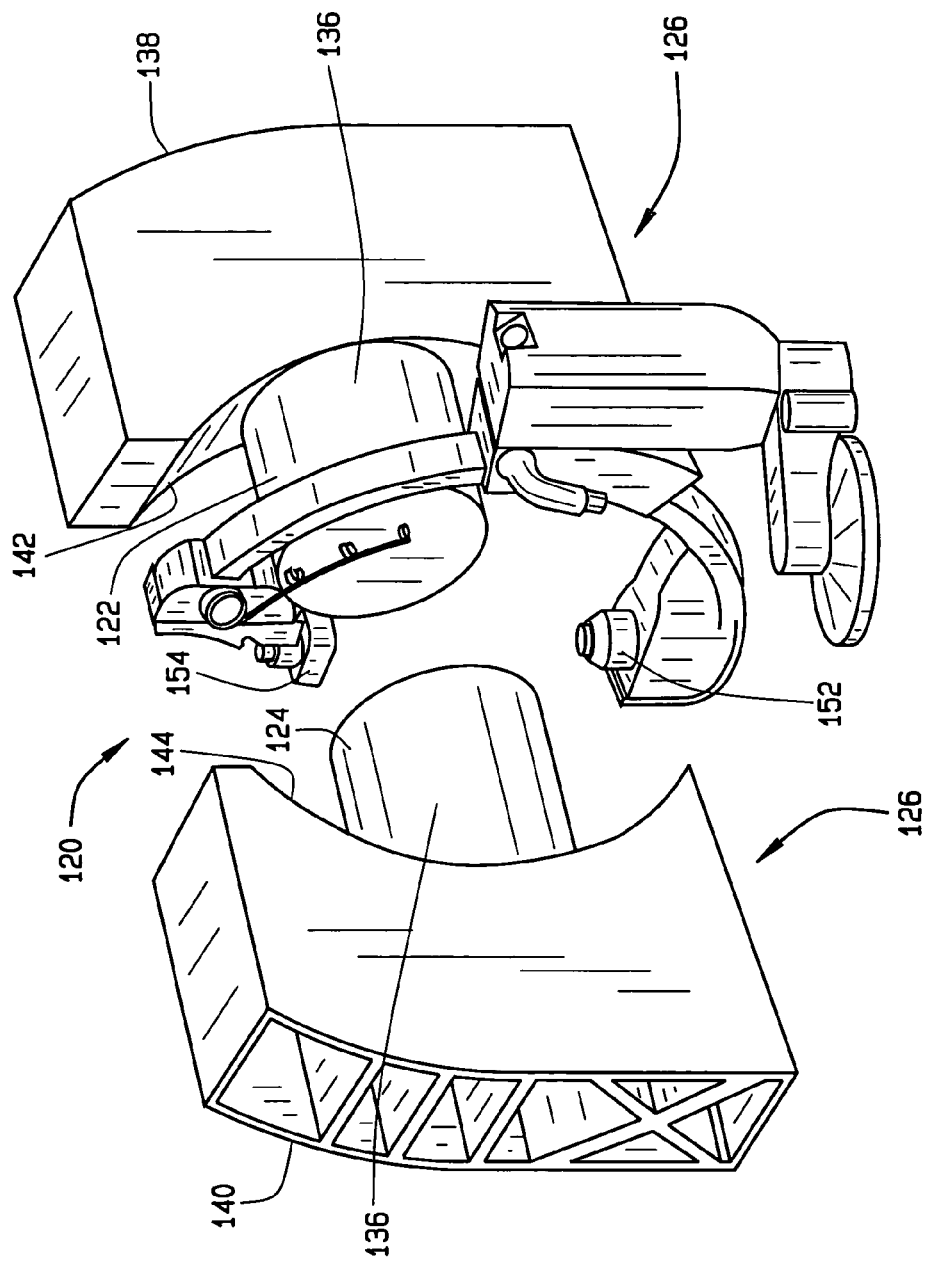
FIG. 7 is a rear perspective view of the magnetic navigation system of the second embodiment.
Figure 8:
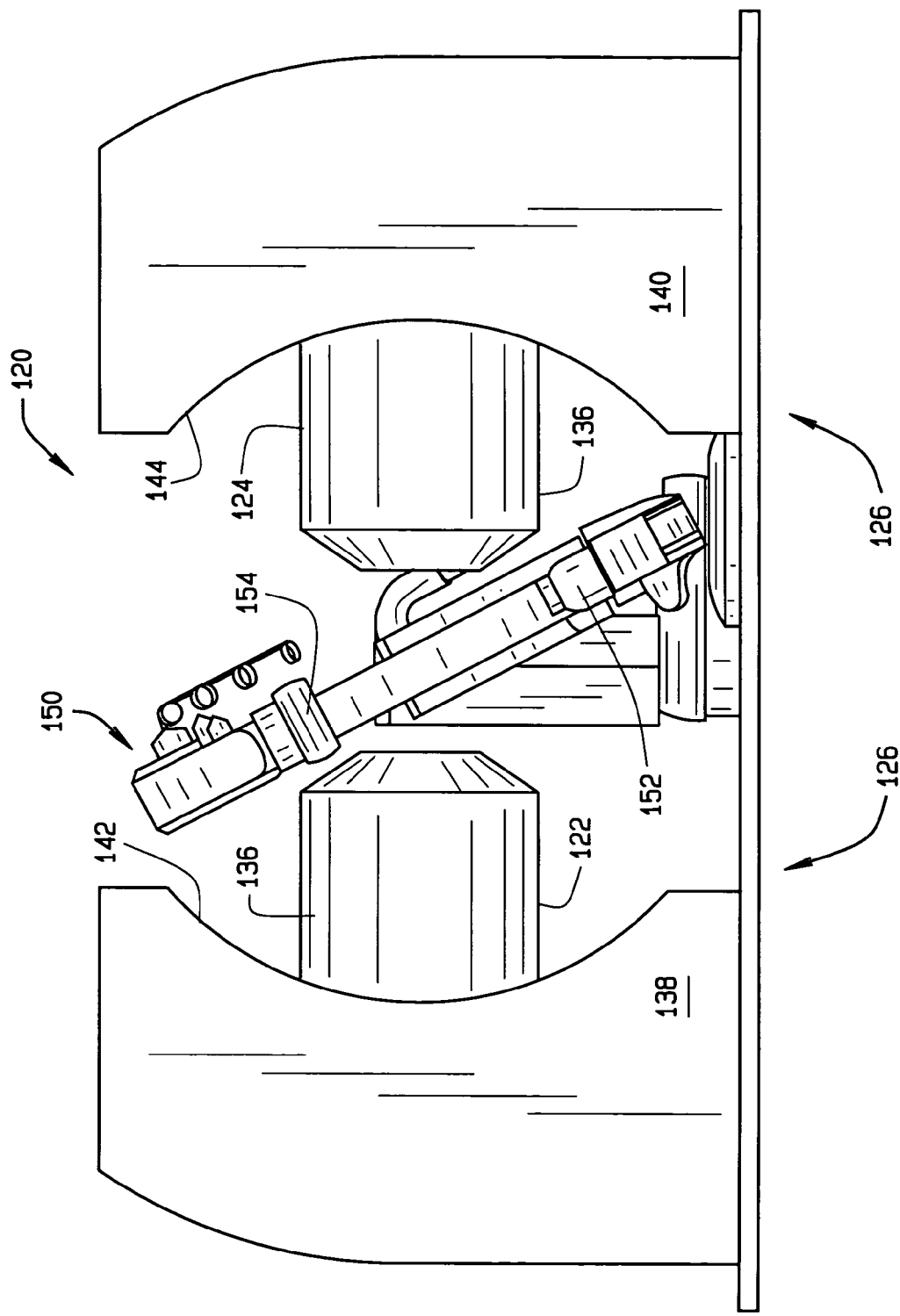
FIG. 8 is a front perspective view of the magnetic navigation system of the second embodiment, with the imaging C-arm rotated 28°.
Figure 9:
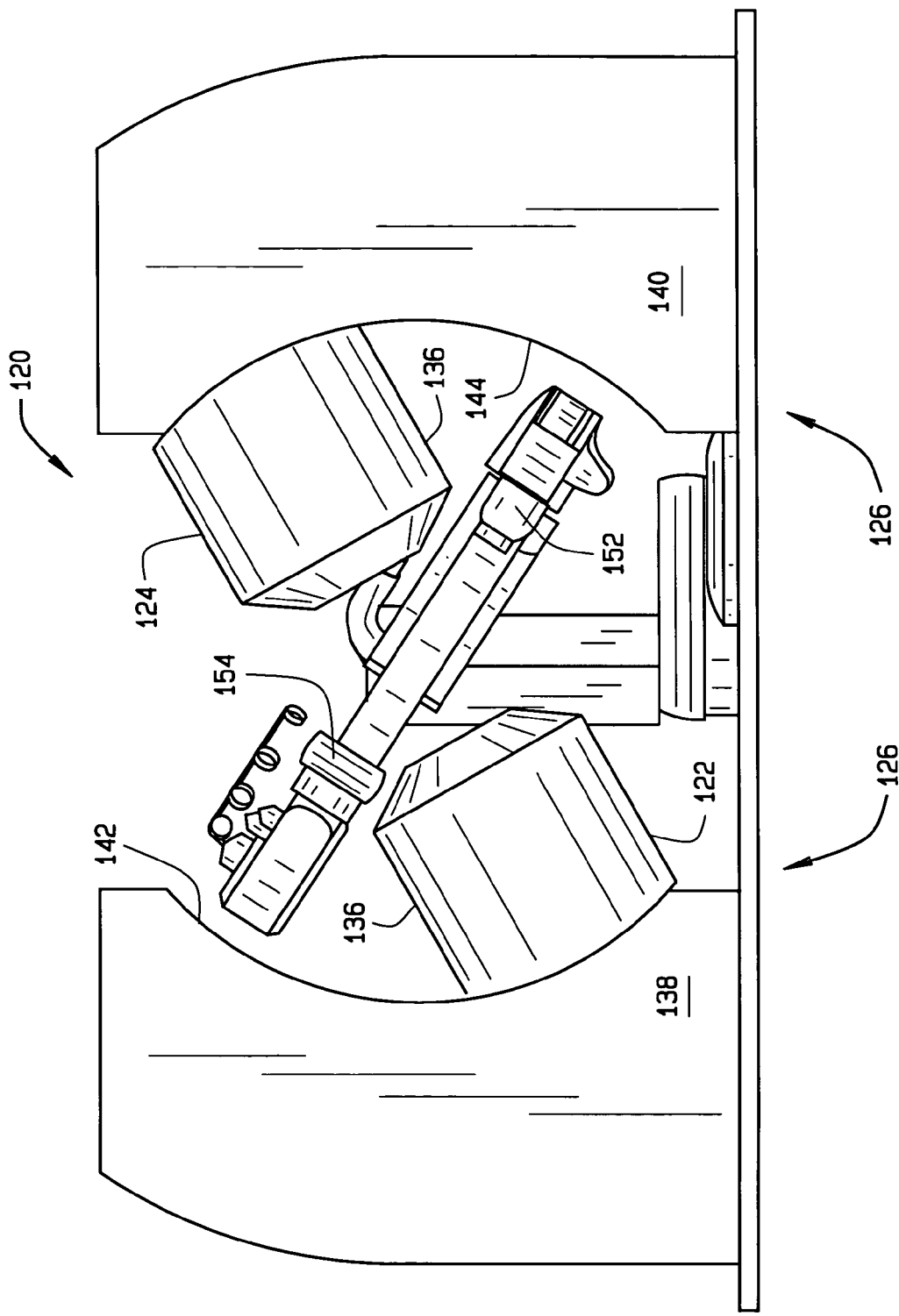
FIG. 9 is a front elevation view of the magnetic navigation system of the second embodiment, with the imaging C-arm rotated 30°, and the magnet units rotated to accommodate the C-arm.

A first embodiment of a magnetic navigation system constructed according to the principles of this invention is indicated generally as 20 in FIGS. 1-4. The system 20 is adapted to apply a magnetic field of selected direction to an operating region in subject on a subject support (not shown) in the magnetic navigation system. The system 20 broadly comprises at least two magnet units 22 and 24 mounted on a support 26 adjacent (and preferably on opposite sides of) the operating region, for coordinated rotational movement about the operating region. The system also includes an imaging system 28 for imaging the operating region.

More specifically, the magnet units 22 and 24 each comprise a compound permanent magnet 30 comprising a plurality of segments of magnetic material with differing magnetization directions so that relatively small rotations or pivots change the magnetic field projected by the magnet at a specific point. Each of the magnet units 22 and 24 also comprise a positioner 32 for controlling the position of the magnet 30, e.g. for rotating the magnet 30 about a first axis and pivoting the magnet 30 about a second axis, to selectively change the magnetic field applied by each magnet to the operating region in a subject on the subject support.

In the preferred embodiments of this invention, the magnet units 22 and 24, and thus their respective magnets 30, are mounted on opposite sides of the operating region. The first axis of rotation of each magnet preferably extends through the respective magnet and the operating region, and preferably the first axes of rotation of the magnets are co-linear. The second axes of pivoting of each magnet is preferably perpendicular to the first axis, and also rotates about the first axis.

Each magnet unit 22 and 24 comprises a cover 36. The cover protects the patient and medical personnel and equipment from the movement of the magnets 30, it hides the movement to prevent patient concern over the operation of the system, and it improves the aesthetics of the system.

As described above, the magnet units 22 and 24 are mounted on opposite sides of the operating region on support 26. This support can be any support that accommodates the coordinated movement of the magnet units 22 and 24 about the operating region. As will be described below in more detail with respect to FIGS. 14A through 14D, it is desirable that the magnets 22 and 24 each rotate through a arc of about 120° from about 60° above the plane of the patient to about 60° below the plane of the patient. Of course, some greater or lesser range of rotation of the magnet units could be provided. One possible configuration for support 26 is shown in FIGS. 1-4, where the support comprises two stanchions 38 and 40, having arcuate surfaces 38 and 40 on which the magnet units 22 and 24 can travel as they rotate about the operating region. The surfaces 40 and 42 can be the arcs of a circle, but could take some other shape so that the distance between the magnet units and the operating region changes as the magnet units rotate about the operating region on the stanchions 38 and 40. Specifically, the surfaces 42 and 44 could be shaped so that the magnet units are closer to the operating region when they are above the plane of the subject. Any drive mechanism can be used to move the magnet units 22 and 24 on the stanchions 38 and 40. Of course, instead of moving the magnet units 22 and 24 on the support, the magnet units 22 and 24 could be fixed relative to the support, and it could be the support that moves to rotate the magnet units 22 and 24 about the operating. In still another alternate construction, the rotation of the magnet units about the operating region could be accomplished by a combination of movement of the magnet units relative to the support, and movement of the support relative to the subject.

The system 20 also includes an imaging system 28 for imaging the operating region. The imaging system preferably includes some type of C-arm structure 50, or some other movable support that allows the imaging equipment to be repositioned about the operating region to allow imaging from the most advantageously angle. For most procedures in the chest, medical personnel are used to have left anterior oblique (lao) and right anterior oblique (rao) images, and the support is preferably capable of moving the imaging equipment to provide these images. The imaging system 28 preferably also includes a imaging beam source 52 and an imaging beam receiver 44, such as an amorphous silicon plate. The source 52 and receiver 54 are preferably constructed to be immune to, or are shielded from the effects of, the magnets 30 in the magnet units 22 and 24.

A control is preferably provided to control the positioners 32 of each magnet unit 22 and 24, to cause the magnets 30 to move to provide a magnetic field in a selected direction in the operating region. An interface can be provided to allow the user to identify a selected magnet field direction, and the controller operates the positioners 32 to position the magnets to achieve the desired magnetic field direction. Alternatively, the interface might allow the user to select a desired medical device orientation, and the controller operates the positioners 32 to position the magnets to achieve the magnetic field direction to achieve the desired medical device orientation. In this latter case the controller may take into account the physically properties of the device, represented in either a look-up table or in a set of equations, or parameters for equations, to determine the field to cause the device to align in the selected direction. The controller might also take into account the field strength applied in the operating region. In many prior magnetic navigation systems, the field strength is relatively constant, however in some embodiments of the present invention, in order to reduce magnet size, and facilitate movement of the magnet units, the field strength might vary depending upon the position of the magnet units. Thus the desired field direction to attain a given device orientation might vary depending upon the position of the magnet units. In at least some embodiments of this invention, the controller determines and applies the field based upon the desired orientation of the medical device input by the user, and upon the strength of the field that the magnets apply in their current position. The controller could also indicate to the user that it would be advantageous to reposition the magnets to achieve a higher field strength.

A second embodiment of a magnetic navigation system constructed according to the principles of this invention is indicated generally as 120 in FIGS. 5-8. The system 120 is adapted to apply a magnetic field of selected direction to an operating region in subject on a subject support (not shown) in the magnetic navigation system. The system 120 broadly comprises at least two magnet units 122 and 124 mounted on a support 126 on opposite sides of the operating region, for coordinated rotational movement about the operating region. The system also includes an imaging system 128 for imaging the operating region.

More specifically, the magnet units 122 and 124 each comprise a compound permanent magnet 30 comprising a plurality of segments of magnetic material with differing magnetization directions so that relatively small rotations or pivots change the magnetic field projected by the magnet at a specific point. Each of the magnet units 122 and 124 also comprise a positioner 132 for controlling the position of the magnet 30, e.g. for rotating the magnet 30 about a first axis and pivoting the magnet 30 about a second axis, to selectively change the magnetic field applied by each magnet to the operating region in a subject on the subject support.

In the preferred embodiments of this invention, the magnet units 122 and 124, and thus their respective magnets 30, are mounted on opposite sides of the operating region. The first axis of rotation of each magnet preferably extend through the respective magnet and the operating region, and preferably the first axes of rotation of the magnets are co-linear. The second axes of pivoting of each magnet is preferably perpendicular to the first axis, and rotates about the first axis.

Each magnet unit 122 and 124 comprises a cover 136, the cover protects the patient and medical personnel and equipment from the movement of the magnets 130, it hides the movement to prevent patient concern over the operation of the system, and it improves the aesthetics of the system.

As described above, the magnet units 122 and 124 are mounted on opposite sides of the operating region on support 126. This support can be any support that accommodates the coordinated movement of the magnet units 122 and 124 about the operating region. As will be described below in more detail with respect to FIGS. 14A through 14D, it is desirable that the magnets 122 and 124 each rotate through a arc of about 120° from about 60° above the plane of the patient to about 60° below the plane of the patient. Of course, some greater or lesser range of rotation of the magnet units could be provided. One possible configuration for support 126 is shown in FIGS. 5-9, where the support comprises two stanchions 138 and 140, having arcuate surfaces 142 and 144 on which the magnet units 122 and 124 can travel as they rotate about the operating region. The surfaces 142 and 144 can be the arcs of a circle, but could take some other shape so that the distance between the magnet units and the operating region changes as the magnet units rotate about the operating region on the stanchions 138 and 140. Specifically, the surfaces 142 and 144 could be shaped so that the magnet units 122 and 124 are closer to the operating region when they are above the plane of the subject. Any drive mechanism can be used to move the magnet units 122 and 124 on the stanchions 134 and 136. Of course, instead of moving the magnet units 122 and 124 on the support, the magnet units 122 and 124 could be fixed relative to the support, and it could be the support that moves to rotate the magnet units 122 and 124 about the operating. In still another alternate construction, the rotation of the magnet units about the operating region could be accomplished by a combination of movement of the magnet units relative to the support, and movement of the support relative to the subject.

The system 120 also includes an imaging system 128 for imaging the operating region. The imaging system preferably includes some type of C-arm structure 150, or some other movable support that allows the imaging equipment to be repositioned about the operating region to allow imaging from the most advantageously angle. For most procedures in the chest, medical personnel are used to have left anterior oblique (lao) and right anterior oblique (rao) images, and the support is preferably capable of moving the imaging equipment to provide these images. The imaging system 128 preferably also includes a imaging beam source 152 and an imaging beam receiver 154, such as an amorphous silicon plate. The source 152 and receiver 154 are preferably constructed to be immune to, or are shielded from the effects of, the magnets 30 in the magnet units 122 and 124.

A control is preferably provided to control the positioners 132 of each magnet unit 122 and 124, to cause the magnets to move to provide a magnetic field in a selected direction. An interface can be provided to allow the users to identify a selected magnet field direction, and the controller operates the positioners 132 to position the magnets to achieve the desired magnetic field direction. Alternatively, the interface might allow the user to select a desired device orientation, and the controller operates the positioners 132 to position the magnets to achieve the desired magnetic field direction to achieve the desired device orientation. In this latter case the controller may take into account the physically properties of the device, represented in either a look-up table or in a set of equations, or parameters for equations, to determine the field to cause the device to align in the selected direction. The controller might also take into account the field strength applied in the operating region. In many prior magnetic navigation systems, the field strength is relatively constant, however in some embodiments of the present invention, in order to reduce magnet size, and facilitate movement of the magnet units, the field strength might vary depending upon the position of the magnet units. Thus the desired field direction to attain a given device orientation might vary depending upon the position of the magnet units. In at least some embodiments of this invention, the controller determines and applies the field based upon the desired orientation of the medical device input by the user, and upon the strength of the field that the magnets apply in their current position. The controller could also indicate to the user that it would be advantageous to reposition the magnets to achieve a higher field strength.

Figure 10:
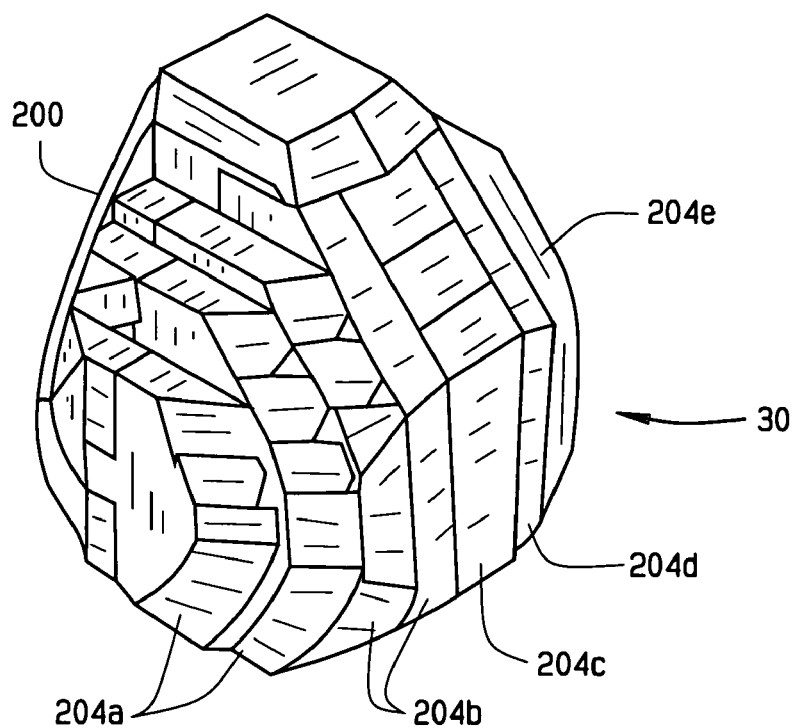
FIG. 10 is a perspective view of a magnet adapted for use in the magnet units of some embodiments of this invention.
Figure 11:
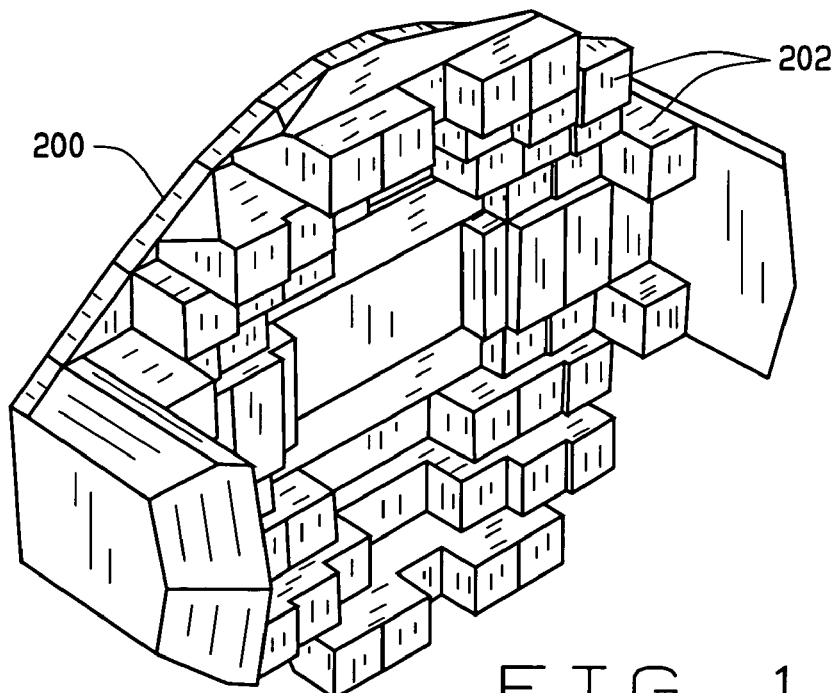
FIG. 11 is a perspective view of a backing plate for a the magnet.
Figure 12:
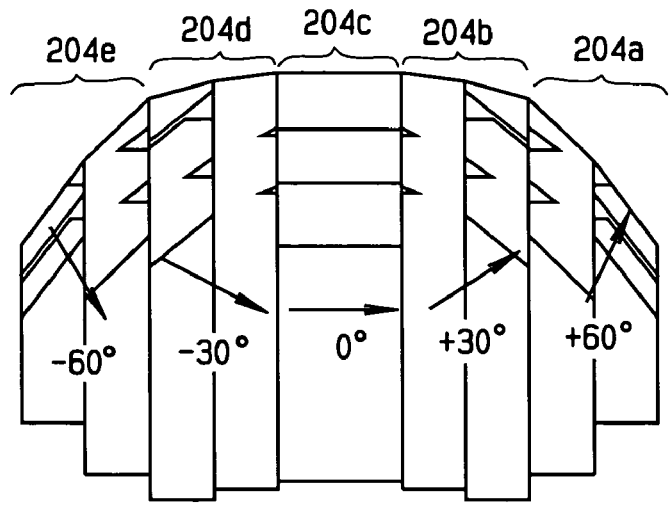
FIG. 12 is a top plan view of the magnet.

As shown in FIGS. 10 and 12, the magnet used in the embodiments of this invention preferably comprises an aluminum backing plate 200, having a plurality of spacer blocks 202 thereon (FIG. 11) for mounting blocks 204 of magnetic material. As described above the blocks 204 are sized, shaped, and positioned, and have a magnetization direction to control the magnetic field strength projected by the assembled magnet into the operating region. Actually, to save manufacturing effort and expense, compromises are made in the shape and magnetization direction of the blocks from the optimum design. The inventors have discovered that a reasonable balance is to provide blocks with five different magnetization directions. Thus, as shown in FIG. 12, the blocks 204a have a magnetization direction of +60° relative to the horizontal axis of the blocks, the blocks 204b have a magnetization direction of +30° relative to the horizontal axis of the blocks, the blocks 204c have a magnetization direction of 0° relative to the horizontal axis, blocks 204d have a magnetization direction of −30° relative to the horizontal axis of the blocks, the blocks 204e have a magnetization direction of −60° relative to the horizontal axis. The blocks are preferably sized, shaped and positioned generally as taught in co-pending application Ser. No. 10/056,227, filed Jan. 23, 2002, for Rotating and Pivoting Magnet for Magnetic Navigation; and application Ser. No. 10/082,715, filed Feb. 25, 2002; for Magnets with Varying Magnetization Direction and Method of Designing Such Magnets; and application Ser. No. 09/546,840, filed Apr. 11, 2000, for Magnets with Varying Magnetization Direction and Method of Designing Such Magnets, the disclosures of which are incorporated herein by reference.

Figure 13A:
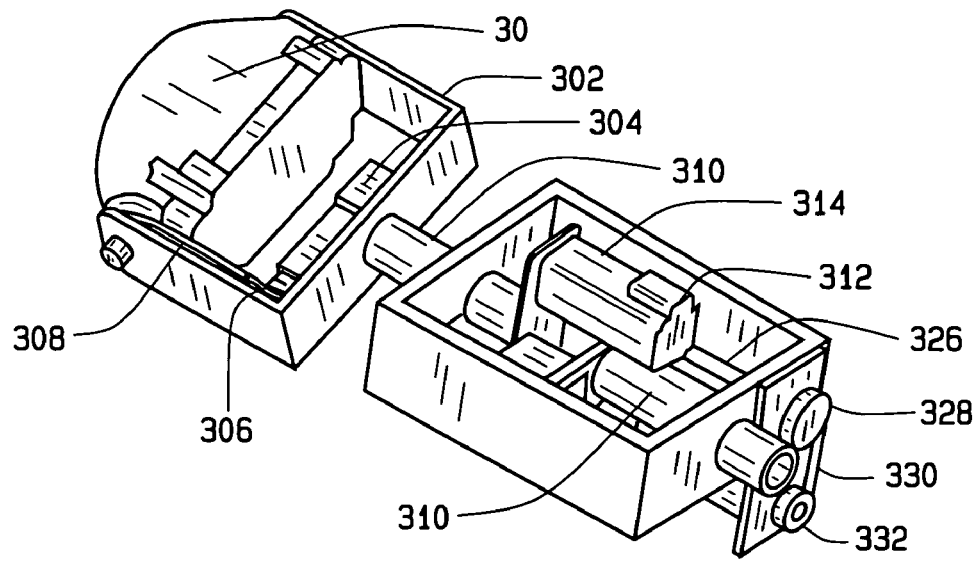
FIG. 13A is a perspective view of a positioner adapted for use in the magnet units of some embodiments of this invention.
Figure 13B:
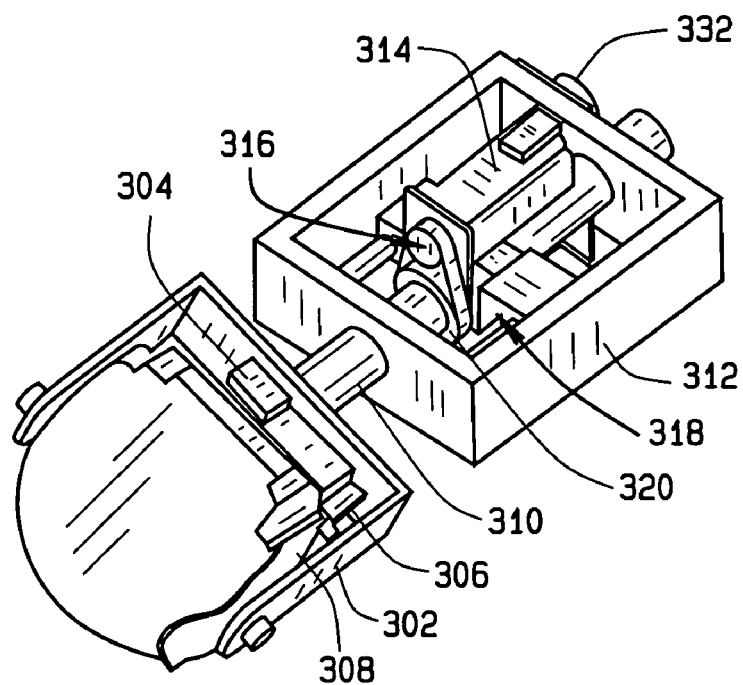
FIG. 13B is a perspective view of the positioner.
Figure 13C:
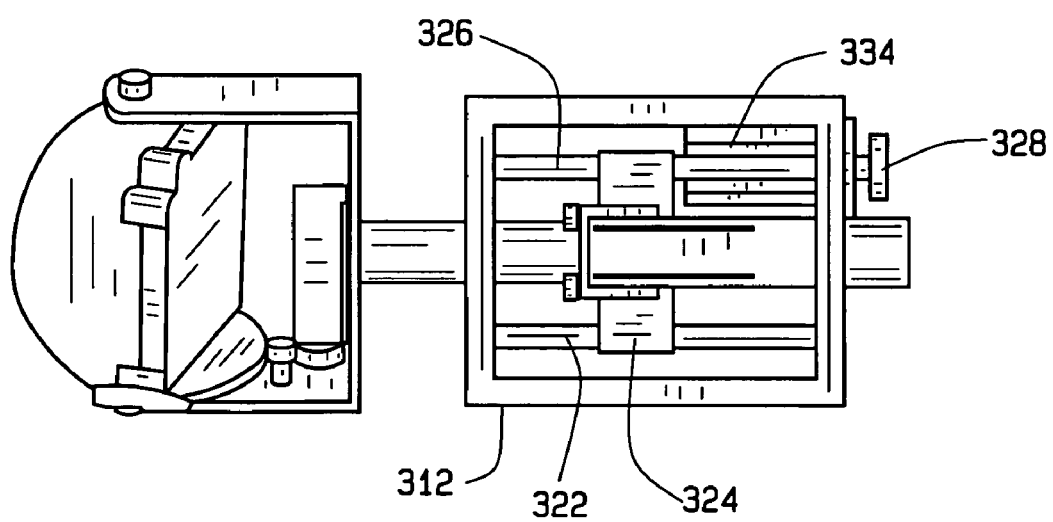
FIG. 13C is a plan view of the positioner.

A positioner 132 adapted for use in some embodiments of the magnetic navigation system of this invention is shown in FIGS. 13A-13C. As shown in FIGS. 13A-13C, the magnet 30 is pivotally mounted between the legs of a generally U-shaped bracket 302. A motor 304 is mounted on the base of the U-shaped bracket, to drive a gear box 306 also mounted on the base of the U-shaped bracket. The gear box 306 drives a cable 308 connected to the magnet 30, so that the motor 304 can move the magnet about its pivotal mounting.

A shaft 310 extends from the bottom of the U-shaped bracket 302, and is rotatably mounted in a box-shaped frame 312. A drive motor 314 drives a sheave 316 which drives a belt 318 that drives a sheave 320 on the shaft 310, to rotate the shaft, and thus the magnet 30. As shown and illustrated in FIGS. 13A-13C, in addition to rotating the magnet about a first axis, and pivoting the magnet about a second, perpendicular axis, the positioner 132 also translates the magnet in a direction generally parallel to the axis of rotation. Thus the positioner 132 includes a guide rod 322, carriage 324 slidably mounted on the guide rod 322, and driven by a lead screw 326. The lead screw 326 has a sheave 328 thereon, and is driven by a belt 330 driven by sheave 332 on motor 334. In other embodiments, the positioner need not be able to translate the magnet, and can merely rotate and pivot the magnet.

Figure 14A:
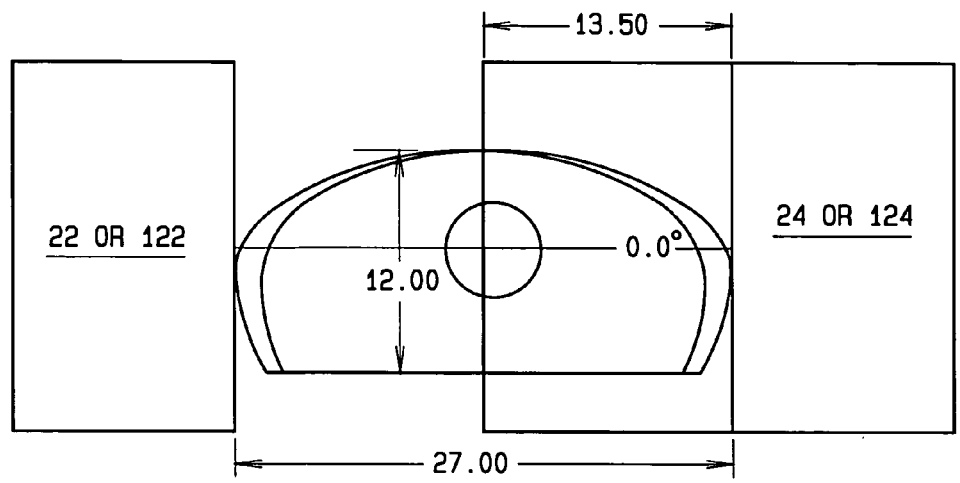
FIG. 14A is a diagram illustrating the positioning of magnets on opposites sides of a patient in the lateral plane.
Figure 14B:
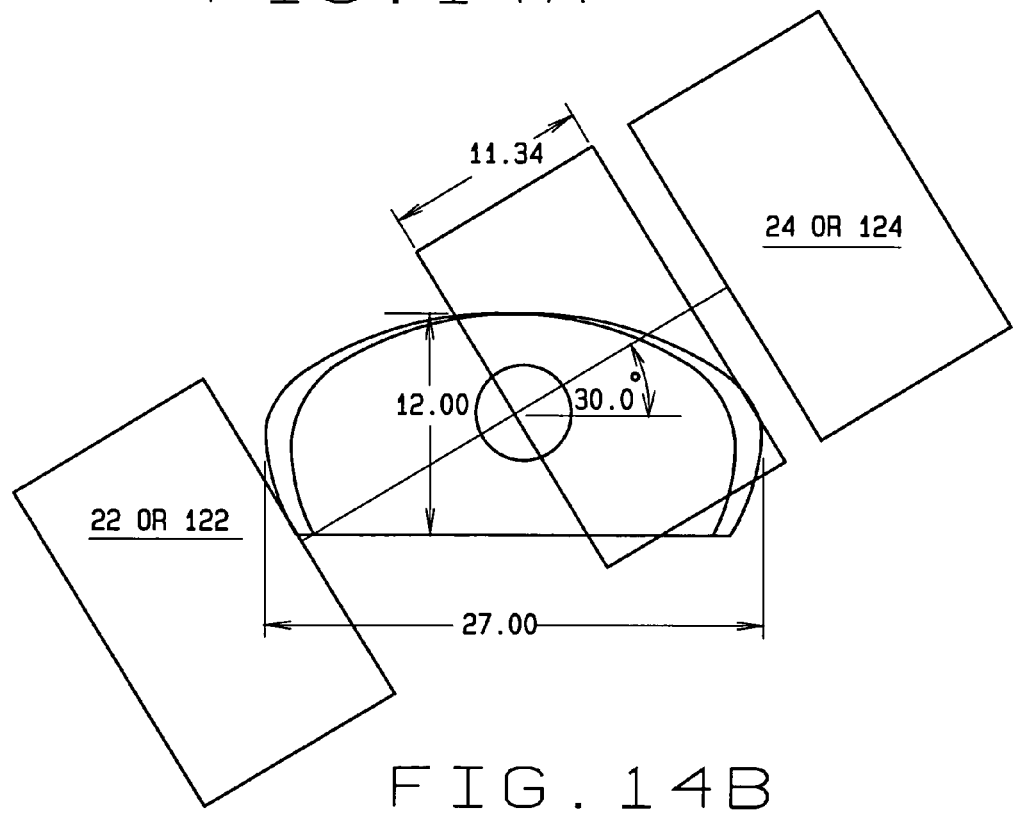
FIG. 14B is a diagram illustrating the positioning of magnets on opposite sides of a patient, rotated 30° in the transverse plane.
Figure 14C:
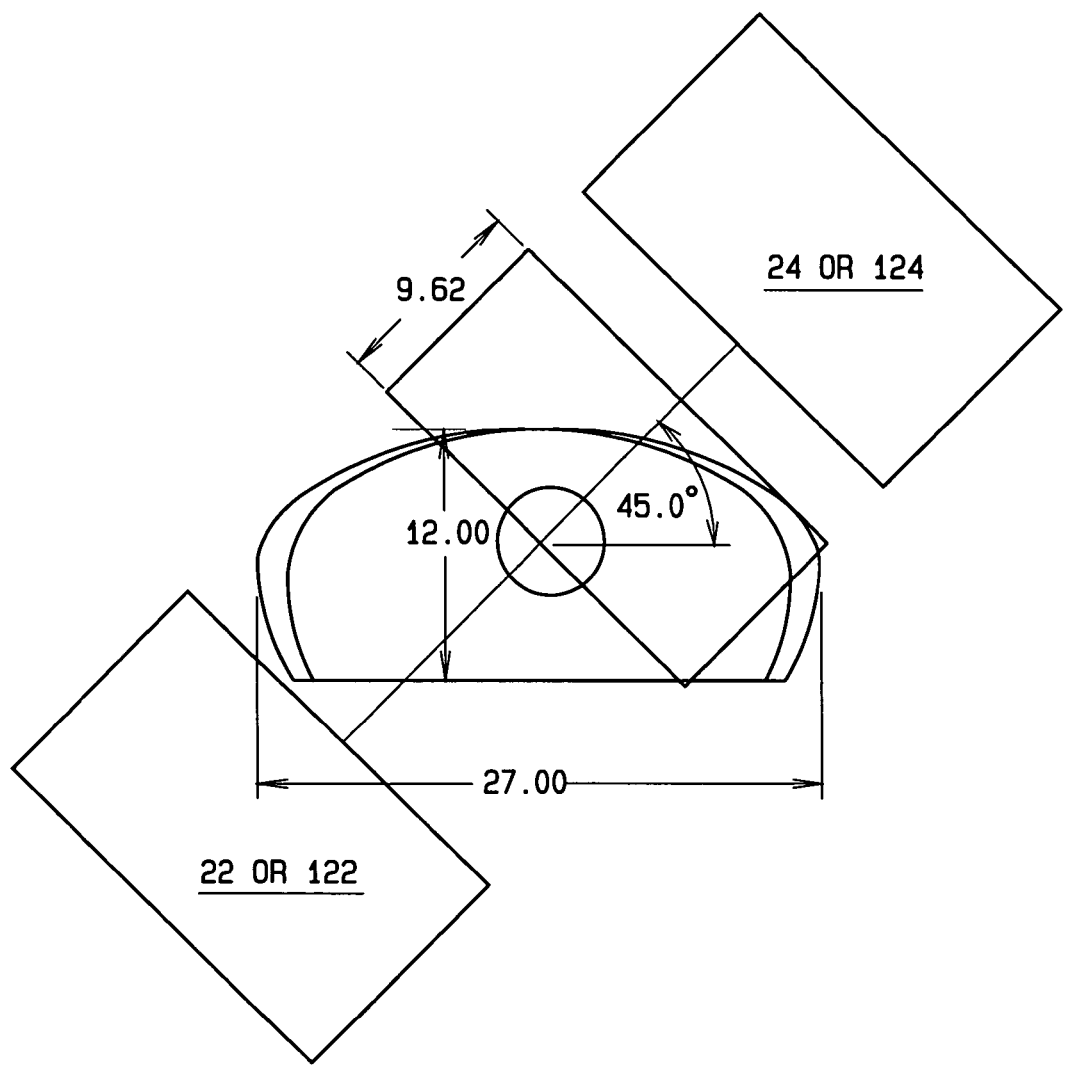
FIG. 14C is a diagram illustrating the positioning of magnets on opposite sides of a patient, rotated 45° in the transverse plane.
Figure 14D:
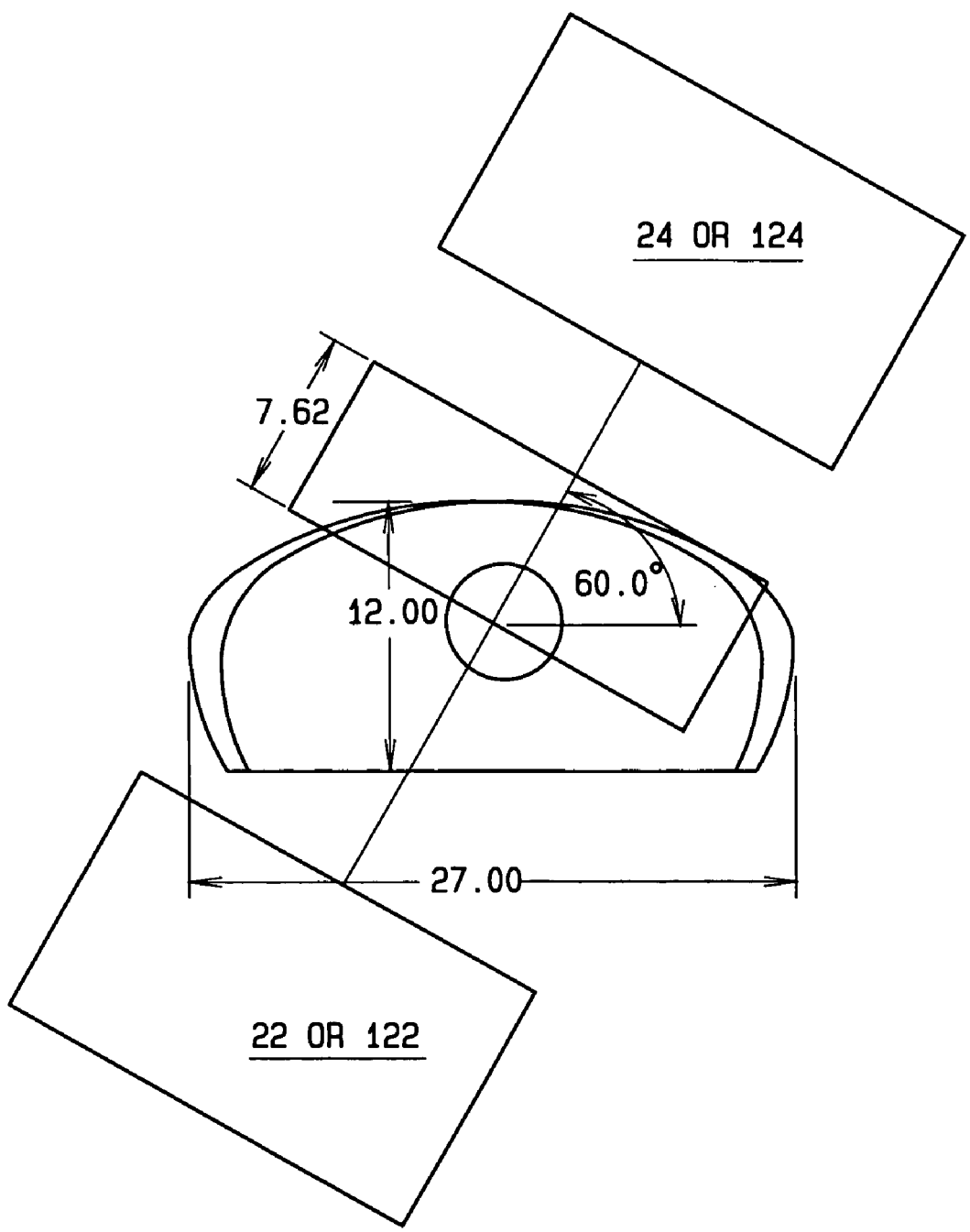
FIG. 14D is a diagram illustrating the positioning of magnets on opposite sides of a patient, rotated 60° in the transverse plane.

As shown in FIGS. 14A-14D, in addition to providing better access to the subject by medical equipment and personnel, the rotating movement of the magnet units also allows the magnet units to be positioned closer to the operating region. As shown in FIG. 14A, when the magnets are disposed in the plane of the patient, the magnets must be spaced sufficiently to accommodate the entire width of the patient. To accommodate most patients, this distance would be a minimum of 27 inches (about 69 cm), which would mean the distance to the center of the patient is 13.5 inches (about 34 cm). If as shown in FIG. 14B, the magnet units are rotated in the transverse plane 30°, at least one of the magnets can be moved closer to the operating region. The magnet unit above the plane of the patient can be moved to a distance of about 11.38 inches (about 29 cm) from the center of the patient. If as shown in FIG. 14C, the magnet units are rotated in the transverse plane 45°, at least one of the magnets can be moved closer to the operating region. The magnet unit above the plane of the patient can be moved to a distance of about 9.57 inches (about 24 cm) from the center of the patient. If as shown in FIG. 14D, the magnet units are rotated in the transverse plane 60°, at least one of the magnets can be moved closer to the operating region. The magnet unit above the plane of the patient can be moved to a distance of about 7.60 inches (about 19 cm) from the center of the patient.

Thus the ability to move the magnet units, allows the magnet units to be placed closer to the patient, allowing smaller magnets to be used. However, when the magnet units have to be moved to provide access to the patient by medical personnel or equipment (e.g. imaging equipment), the magnets can be moved out of the way, while maintaining the magnetic field in the same direction (or in some preferred embodiments, adjusting the magnetic field direction to accommodating the changing field strength in the operating region).

What is claimed is:

1. A method comprising: controlling
magnets in two magnet units disposed on opposite sides of a subject, the magnet units including a magnet and a positioner for rotating the magnet about a first axis and pivoting the magnet about a second axis, the magnet units being movably mounted on a support for movement about the subject, and the magnets being positioned to project a magnetic field in a direction to orient a magnetically responsive medical device in a selected direction, the method further comprising selectively rotating and pivoting each magnet to maintain the magnetic field direction projected by the moving magnets in relation to the magnetically responsive medical device as the magnet units move on the support about an operating region of the subject to maintain the magnetically responsive medical device in a selected orientation as the units move on the support.

2. The method according to claim 1 further comprising coordinating the movement of the magnet units with an imaging system to avoid positional interference between the imaging system and the magnet units.

3. The method according to claim 1 further comprising adjusting the positions of the magnets in the magnet units while moving the magnet units to accommodate movements of an imaging system to maintain the desired orientation of the medical device.

4. The method according to claim 1 wherein the positions of the magnets are adjusted as the magnet units move to change the direction of the magnetic field applied by the magnet units to maintain the device in substantially the selected direction despite changes in the distance between the magnet units and the operating region.

5. The method according to claim 4 wherein the direction of the magnetic field applied by the magnet units is determined based upon a mathematical model.

6. The method according to claim 4 wherein the direction of the magnetic field applied by the magnet units is determined based upon a lookup table.

7. The method of claim 1, wherein the magnet units on the support are disposed on opposite sides of a subject in a generally opposed relation to apply the magnetic field to the operating region of the subject, the method further comprising the controlled rotation of the magnet units about the subject to maintain the magnet units in opposed relation.

8. The method of claim 1, further comprising controlling the positioners of each of the magnet units to change the positions of the magnets a user-input selected magnetic field direction.

9. The method of claim 1, further comprising controlling the positioners of each of the magnet units to change the positions of the magnets in response to a user-input selected direction to apply the magnetic field in the operating region to cause the magnetically responsive device to orient substantially in the selected direction.

10. The method of claim 1, further comprising controlling the positioners of each of the magnet units to change the positions of the magnets as the magnet units move in order to maintain the magnetic field direction.

11. The method according to claim 9 wherein the controller controls the positioners in response to movement of the magnet units, to apply a field whose direction is determined based upon a user-selected direction and a strength of the field in the operation region.

12. The method according to claim 1 wherein the support is generally arcuate and mounts the magnet units for arcuate movement in a plane generally transverse to a longitudinal axis of the subject support.

13. The system method according to claim 1 wherein the support comprises first and second stanchions disposed on opposite sides of the subject, each stanchion having an arcuate track, and mounting one of the units for coordinated movement about an arcuate path, so that the magnet units remain opposite one another.

14. The system method according to claim 1 wherein the first axes of the magnet units are parallel.

15. The method according to claim 1 wherein the first axes of the magnet units are collinear and extend through the operating region.

* * * * *